United States Patent [19]

Butler

[11] 4,179,563

[45] Dec. 18, 1979

[54] 3-ARYLOXY-SUBSTITUTED-AMINOPYRIDINES AND METHODS FOR THEIR PRODUCTION

[75] Inventor: Donald E. Butler, Ann Arbor, Mich.

[73] Assignee: Warner-Lambert Company, Morris Plains, N.J.

[21] Appl. No.: 907,422

[22] Filed: May 19, 1978

[51] Int. Cl.$^2$ .................. A61K 31/44; A61K 31/505; C07D 213/65; C07D 401/04
[52] U.S. Cl. .................. 544/360; 424/244; 424/250; 424/263; 546/297; 260/244.4
[58] Field of Search .................. 424/244, 250, 263; 544/360; 260/239 BC, 296 R, 244.4; 546/276, 297

[56] References Cited

U.S. PATENT DOCUMENTS

| | | | |
|---|---|---|---|
| 4,029,790 | 6/1977 | Mauvernay et al. | 544/360 |
| 4,078,063 | 3/1978 | Lumma et al. | 544/360 |

*Primary Examiner*—Alton D. Rollins
*Assistant Examiner*—James H. Turnipseed
*Attorney, Agent, or Firm*—David B. Ehrlinger; Frank S. Chow; Stephen Raines

[57] ABSTRACT

3-Aryloxy-substituted-aminopyridines and salts thereof, which are useful as pharmacological agents, especially cognition activators, are disclosed. They can be produced by reacting a chloro-3-aryloxypyridine with a substituted amine, 3-bromo-substituted-aminopyridine with an alkali metal salt of a phenol compound or by deoxygenation of a 3-aryloxy-substituted-aminopyridine N-oxide.

8 Claims, No Drawings

3-ARYLOXY-SUBSTITUTED-AMINOPYRIDINES AND METHODS FOR THEIR PRODUCTION

SUMMARY AND DETAILED DESCRIPTION

The present invention relates to new 3-aryloxy-substituted-aminopyridine compounds. More particularly, the invention relates to new 3-aryloxy-substituted-aminopyridine compounds of the formula

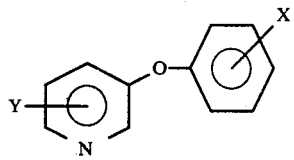   I and acid addition salts thereof, and to a method for the production of the foregoing compounds; where X is hydrogen, fluorine or chlorine and Y is 1-piperazinyl, 3-methyl-1-piperazinyl, hexahydro-4-methyl-1H-1,4-diazepin-1-yl, anilino, or 2-[di(lower alkyl)amino]-ethylamino.

The preferred compounds are those wherein X is hydrogen, Y is piperazinyl, diethylamino-ethylamino or anilino and the Y substituent is in the 4 or 2 position.

The term "lower alkyl" is intended to mean an alkyl group of from one to four carbon atoms.

The term "acid addition salts" are intended to mean salts formed by the addition of an acid. Typical salts are as follows: pamoate, acetate, citrate, hydrochloride, dihydrochloride, sulfate, phosphate, benzoate, hydrobromide, nitrate, citraconate, maleate, methanesulfonate, etc. Pharmaceutically acceptable acid addition salts are preferred.

In accordance with the invention, the foregoing compounds of formula I can be prepared by reacting a compound of the formula

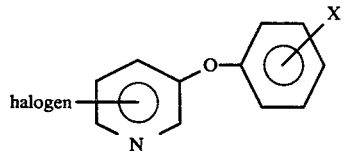   II with a compound of the formula

YH   (III)

in the presence of a base wherein X and Y are as previously defined and halogen is chlorine, bromine, iodine or fluorine, preferably chlorine.

Although equimolar quantities of reactants may be used, it is preferred to employ a moderate to large excess of the amine which can also serve as the base. Most any base such as potassium carbonate, sodium carbonate, calcium hydroxide and sodium bicarbonate may be used as an acid acceptor in the reaction.

The reaction may be carried out in most any organic solvent, which would include; lower alcohols such as ethanol, n-butanol; hydrocarbons such as benzene, toluene and xylene; ethers such as dioxane and diethylene glycol dimethyl ether; acetonitrile; dimethyl sulfoxide; N-methylpyrrolidone and N-methylpiperidone and mixtures of these. When YH is a liquid, an excess of this amine can also be used in place of solvent. N-butanol or the liquid amines are preferred.

The reaction is carried out at a temperature range of 50° to 200° C. for periods of from one to 72 hrs, preferably 80° to 120° C. for from 16 to 24 hrs.

The product may be isolated as the free base by distillation or crystallization or as an acid-addition salt by suitable adjustment of the pH.

While most of the starting materials are known compounds and the remainder are prepared by standard laboratory methods, the method of preparation of a number of starting materials is shown in another part of the specification.

Also in accordance with the invention, the foregoing compounds of formula I can be prepared by reacting a compound of the formula

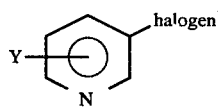   IV with a compound of the formula

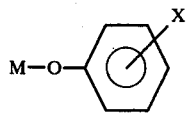   V in the presence of a catalyst, such as finely divided copper powder or copper bronze powder, Y and X are as previously defined and wherein halogen is bromine or chlorine, preferably bromine and M is an alkali metal, preferably potassium. Although equimolar quantities of reactants IV and V may be used, it is preferred to employ a moderate to large excess of the alkali metal phenolate salt.

Most typical organic solvents may be used as a reaction medium including an excess of the phenol from which the compound formula V generated. Other solvents are ethers, such as diethylene glycol dimethyl ether, triethylene glycol dimethyl ether, N-methylpyrrolidone, N-methylpiperidone or mixtures of these. A preferred solvent is an excess of the phenol.

The reaction is carried out at a temperature range of from 150° to 250° C. for periods of from one to 24 hrs, preferably 160° to 200° C. for about 16 hrs.

The product may be isolated as the free base by distillation or crystallization or as an acid-addition salt by suitable adjustment of the pH.

While most of the starting materials are known compounds and the remainder are prepared by standard laboratory methods, the method of preparation of a number of starting materials is shown in another part of the specification.

Lastly, the foregoing compounds of formula I can be prepared by catalytically reducing a compound of the formula

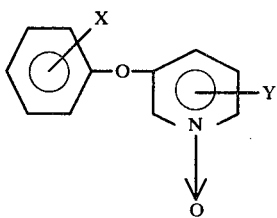

using hydrogen in the presence of a noble metal catalyst, where X and Y are as previously defined. The noble metal catalyst is preferably platinum or palladium and the finely divided catalysts are generally employed on a support, preferably carbon black (20% palladium-on-carbon).

While small quantities of catalyst are employed, large excesses of hydrogen are used when compared to the amount of compound of formula VI.

The reaction is carried out generally in a pressurized vessel using an organic solvent.

The type solvents include lower alcohols, such as methanol, ethanol, n-butanol; alkanoic acids, such as acetic acid, propionic acid or dichloromethane in a lower alcohol. The preferred solvents are acetic acid or ethanol.

The reaction is carried out at a temperature of from 10° to 100° C., preferably 25° C. until the theoretical amount of hydrogen has been absorbed, usually 1 to 24 hrs.

The product may be isolated as the free base by distillation or crystallization or as an acid-addition salt by suitable adjustment of the pH. The hydrochloride can be isolated directly if sufficient dichloromethane is present to give the hydrochloride.

A method for preparing the starting materials of formula VI is shown in another part of the specification.

The compounds of the invention can exist in anhydrous form as well as in solvated, including hydrated, forms. In general, the hydrated forms and the solvated forms with pharmaceutically-acceptable solvents are equivalent to the anhydrous or unsolvated form for the purposes of the invention.

Also in accordance with the invention, pharmaceutical compositions may be produced by formulating the compounds of formula I or a pharmaceutically acceptable acid-addition salt thereof in dosage unit form with a pharmaceutical carrier. Some examples of dosage unit forms are tablets, capsules, lozenges, and pills; as well as powders and aqueous and non-aqueous solutions and suspensions packaged in containers containing either one or some larger number of dosage units and capable of being sub-divided into individual doses by such means as measurement into teaspoon or other standard container. Some examples of suitable pharmaceutical carriers, including pharmaceutical diluents, are gelatin capsules; sugars such as lactose and sucrose; starches such as corn starch and potato starch; cellulose derivatives such as sodium carboxymethyl cellulose, ethyl cellulose, methyl cellulose, and cellulose acetate phthalate; gelatin; talc; stearic acid; magnesium stearate; vegetable oils such as peanut oil, cottonseed oil, sesame oil, olive oil, corn oil, and oil of theobroma; propylene glycol; glycerine, sorbitol; polyethylene glycol; water; agar; alginic acid; as well as other compatible substances normally used in pharmaceutical formulations. The compositions of the invention can also contain other components such as coloring agents, flavoring agents, and/or preservatives. These materials, if present, are usually used in relatively small amounts. The compositions can, if desired, also contain other therapeutic agents.

The percentage of the active ingredient in the foregoing compositions can be varied within wide limits but for practical purposes it is preferably present in a concentration of at least 10% in a solid composition and at least 2% in a primarily liquid composition. The most satisfactory compositions are those in which a much higher proportion of the active ingredient is present. The compositions of the invention preferably contain from 1 to 500 mg, preferably 5 to 100 mg of the active ingredient per dosage unit so that the entire amount to be administered during a day can be made up from a reasonable number of dosage units.

The compounds of formula I and pharmaceutically acceptable acid addition salts may be incorporated into formulations intended for parenteral administration. Such compositions may be in a powdered form intended to be combined with an isotonic solution containing other ingredients such as preservatives, etc. or may be initially formulated as part of an isotonic solution which may contain preservatives, other active ingredients, etc. The compounds of the invention are new chemical compounds of value as pharmacological agents. More specifically, they are cognition activators which are potentially useful in treating patients suffering from senility. The compounds also find use in the treatment of induced amnesia. In addition, the alerting and attention focusing quality of these compounds would make them useful in treating patients having certain learning disabilities. The compounds of the invention generally would be administered to mammals in a dosage range of from about 1 to about 20 mg per kg of body weight per day, preferably 3 to 10 mg per kg per day. Thus 70 mg to 1400 mg, preferably 210 mg to 700 mg, are administered to a 70 kg host per day.

The effectiveness of the aforementioned compounds is determined by the following tests. The first test is a modification of a learning and memory (LM) test procedure which is generally described in "Psychological Reports", 14, 731 (1964) and "Science", 178, 518 (1972) (results shown in Table 1). The modifications are described in U.S. Pat. No. 4,067,983, Jan. 10, 1978. The second test (LMC) given below is designed to show the compound's ability to reverse amnesia produced by electroconvulsive shock (results shown in Table 2). Compounds exhibiting activity in either test are deemed to be useful as cognition activators.

One hundred male mice (Carworth, CF-1 strain, 19–21 g at time of shipment) are divided into five groups of 20 mice each. Each mouse is placed, one at a time, on a small shelf attached to the outside wall of a test box. In this position the mouse is suspended in space. Therefore, the mouse is motivated to step from the shelf through a conveniently placed small hole into the interior of the box. As soon as the mouse has all four feet within the semidarkened interior of the box, the grid floor of the box is electrified (1.5 milliamps, 3 second duration) to produce a strong pain-fear reaction from the animal. About five seconds thereafter, the mouse is removed from the test box and placed in a group holding cage.

Two hours after the above training the mice are given a single electro-convulsion shock produced by 20 milliamps delivered for 0.5 seconds through the ears. Immediately thereafter, the mice are returned to the holding cage.

Two hours after the convulsive treatment, the mice are injected intraperitoneally with the chemical being assessed. Usually three doses of the chemical will be tested at a time.

One hour after the drug treatment, the mice are tested for memory of the painful foot shock received within the shelf-box apparatus. This testing is accomplished by once again placing each mouse on the small shelf attached to the test box. Any mouse that stays on the shelf for 60 seconds without entering the box is counted as remembering the painful foot shock received within the box five hours earlier. Any mouse entering the box within the 60-second period is counted as having amnesia for the painful event.

Using this 60-second criterion, appropriate control experiments show (1.) 100 percent of mice will enter the box if no foot shock is delivered during the original training, (painful foot shock is necessary if the mice are to develop an aversion to entering the text box) (2.) 100 percent of mice will enter the box under the foregoing conditions even when treated with electroconvulsive shock at the three-hour point prior to testing (electroconvulsive shock treatment itself does not generate a fear of entering the test box).

The five groups of mice are treated as follows:

| Group | Treatments |
|---|---|
| (1) Ceiling Control Group: | Placebo |
| (2) Base Line Control Group: | Electroconvulsive shock, Placebo |
| (3) 1st Drug Dose Group: | Electroconvulsive shock, 3-aryloxy-2(4,5 or 6) substituted aminopyridines. |
| (4) 2nd Drug Dose Group: | Electroconvulsive shock, 3-aryoxy-2(4,5 or 6) substituted aminopyridines. |
| (5) 3rd Drug Dose Group: | Electroconvulsive shock, 3-aryloxy-2(4,5 or 6) substituted aminopyridines. |

The percentage of amnesia reversal is determined as follows for each drug group:

percent amnesia reversal = $\frac{\text{Drug group} - \text{Base line control group}}{\text{Ceiling control group} - \text{Base line control group}} \times 100$ The following criteria is used in interpreting the percent of amnesia reversal scores:

40 percent or more (active=A) 25 to 39 percent (borderline=C) and 0 to 29 percent (inactive=N). The duration of the electroconvulsive shock can be varied making the test more or less difficult for a compound to demonstrate an A or C rating. Thus a compound with activity in senile patients and in patients with early memory defects, Piracetam ® [Acta Psychiac. Scand. 54, 150 (1976)], has been administered in this test using the above methodology and 0.2 second and 0.5 second electro-convulsive shock and gave the following results.

| Piractam ®(mg/kg) | 0.2 sec ECS | 0.5 sec ECS |
|---|---|---|
| 80 | C | N |
| 20 | A | N |
| 5 | C | N |

The inverted U shaped dose response curve is typical of this type of agent.

The following tables report the results for certain compounds of the invention.

Table I

| | LM test Dose Levels (mg/kg) | | | | | | | | |
|---|---|---|---|---|---|---|---|---|---|
| Compound | 0.31 | 0.63 | 1.25 | 2.5 | 5.0 | 10. | 20. | 40. | 80. |
| Example | | | | | | | | | |
| 1 | N | C | C | A | N | A | A | C | N |
| 2 | | N | N | N | C | | N | | N |
| 4 | | | | N | | | N | | N |
| 5 | | N | N | C | N | | N | | N |
| 6 | | | N | C | N | A | N | C | C |
| 7 | | | | N | | | N | | N |
| 8 | | C | A | N | | | | | |

Table II

| | LMC test Dose Levels (mg/kg) | | | | | | | | |
|---|---|---|---|---|---|---|---|---|---|
| Compound | 0.31 | 0.63 | 1.25 | 2.5 | 5.0 | 10. | 20. | 40. | 80. |
| Example | | | | | | | | | |
| 1 | | | | C | A | A | A | N | |
| 2 | | | C | A | A | N | N | | |
| 3 | | | | C | | A | | | N |
| 4 | | | N | N | N | A | A | A | N |
| 5 | | | | | N | A | A | C | |
| 6 | | | | N | N | N | N | N | |
| 7 | | | | C | N | A | | | |
| 9 | | N | N | N | A | | A | | C |
| 10 | | | | | A | | A | | C |
| 11 | | | | | C | A | N | C | |
| 12 | | N | N | C | A | N | | | |
| 13 | | | | | N | | A | | C |
| 14 | | | | | N | | C | C | A |
| 15 | | | | C | N | | A | | N |
| 16 | | N | A | N | C | | C | | N |
| 17 | A | A | A | A | A | A | N | | N |
| 18 | | | | | N | | A | | A |
| 19 | | | | | N | | A | A | A |
| 20 | | | | | N | | C | | A |
| 21 | | N | A | C | N | N | | | |

EXAMPLE 1

3-Phenoxy-4-piperazinylpyridine and dihydrochloride

To a solution of 13 g of 4-chloro-3-phenoxypyridine in 25 ml of methanol is added 30 g of piperazine and the solution is stirred and heated for 72 hours. The resulting mixture is concentrated at reduced pressure. The residue is shaken with 500 ml of ether and excess dilute aqueous sodium hydroxide. The organic phase is separated, dried and filtered. The filtrate is concentrated and the product distilled to give 3-phenoxy-4-piperazinylpyridine; bp 134°–135° C./0.2 mm, solidified and has a mp of 74°–77° C.

A solution of this free base in 2-propanol is treated with a slight excess of dry hydrogen chloride. The resulting precipitate of dihydrochloride is collected by filtration; mp 223°–226° C. dec after crystallization from methanol.

EXAMPLE 2

3-Phenoxy-2-piperazinylpyridine

To a solution of 10.5 g of 2-chloro-3-phenoxypyridine in 25 ml of n-butanol is added 20 g of piperazine and the solution is refluxed for 24 hours. The resulting mixture is concentrated at reduced pressure. The residue is shaken with 500 ml of ether and excess dilute aqueous sodium hydroxide. The organic phase is separated, dried and filtered. The filtrate is concentrated and the product distilled to give 3-phenoxy-2-piperazinylpyridine; bp, 115°–117° C./0.15 mm, crystallized and has a mp 56°–59° C.

EXAMPLE 3

6-(β-diethylaminoethylamino)-3-phenoxypyridine

To a solution of 3.9 g 6-chloro-3-phenoxypyridine in 5 ml n-butnaol, is added 22 g β-diethylaminoethylamine and the solution is refluxed for 72 hours. The mixture is concentrated at reduced pressure. The residue is shaken with 500 ml dichloromethane and excess dilute sodium hydroxide. The organic phase is separated, dried and distilled; bp 115°–145° C./0.1 mm. The oil is chromatographed over 150 g basic alumina (Woelm, grade I) in toluene and eluted with 0.4% MeOH in toluene. The fractions containing pure product are combined, concentrated and distilled to give 6-(β-diethylaminoethylamino)-3-phenoxypyridine; bp 143°–145° C./0.1 mm.

EXAMPLE 4

3-Phenoxy-6-piperazinylpyridine

To a solution of 40 g of phenol in 100 ml toluene is added 15 g of potassium tertiary butoxide and the low boiling solvents are distilled until the temperature of the residue reaches 180° C. To the residue is added 25 g of 3-bromo-6-piperazinylpyridine and 0.5 g of finely divided copper bronze powder. The mixture is heated and stirred at 200° C. for 18 hours. The mixture is diluted with 500 ml of toluene and filtered through an inert filter aid. The organic phase is washed thoroughly with a large excess of 25% sodium hydroxide solution, filtered, concentrated and distilled to give 3-phenoxy-6-piperazinyl pyridine; bp 148°–150° C./0.15 mm; m.p. 80.5°–83° C. after recrystallization from n-heptane.

EXAMPLE 5

4-Anilino-3-phenoxypyridine

By substituting 40 g of aniline for the piperazine in Example 1, the product is 4-anilino-3-phenoxy-pyridine; m.p. 111°–113° C.

EXAMPLE 6

2-Anilino-3-phenoxypyridine

By substituting 20 g of aniline for the piperazine in Example 2, the product is 2-anilino-3-phenoxy-pyridine; bp 143°–145° C./0.2 mm.

EXAMPLE 7

4-(3-methylpiperazinyl)-3-phenoxypyridine

By substituting 30 g of 2-methylpiperazine for the piperazine in Example 1, the product is 4-(3-methylpiperazinyl)-3-phenoxypyridine; mp 55°–57° C. after recrystallization from anhydrous ether.

EXAMPLE 8

4-(Hexahydro-4-methyl-1H-1,4-diazepin-1-yl)-3-phenoxypyridine

By substituting 30 g of hexahydro-1H-1,4-diazepine for the piperazine in Example 1, the product is 4-(hexahydro-1H-1,4-diazepin-1-yl)-3-phenoxy pyridine, bp 143°–145° C./0.13 mm). Three and four tenths g of this material is dissolved in a mixture of 4.5 g 37% formalin and 2 ml of methanol and is treated with 6 g of 97–100% formic acid. The mixture is heated at 100° C. for 18 hours. The mixture is cooled, treated with an excess of dilute hydrochloric acid and concentrated in vacuo. The residue is shaken with 100 ml of toluene and excess dilute aqueous sodium hydroxide. The organic phase is dried, concentrated and distilled to give 4-(hexahydro-4-methyl-1H-1,4-diazepin-1-yl)-3-phenoxypyridine; bp 130°–131° C./0.1 mm.

EXAMPLE 9

3-(p-Chlorophenoxy)-2-piperazinylpyridine

By substituting 6 g of 2-chloro-3-(p-chlorophenoxy)-pyridine for the 2-chloro-3-phenoxypyridine in Example 2, the product is 3-(p-chlorophenoxy)-2-piperazinylpyridine; bp 142°–145° C./0.1 mm.

EXAMPLE 10

3-(o-Fluorophenoxy)-2-piperazinylpyridine

By substituting 5 g of 2-chloro-3-(o-fluorophenoxy)-pyridine for the 2-chloro-3-phenoxypyridine in Example 2, the product is 3(o-fluorophenoxy)-2-piperazinylpyridine; bp 122°–133° C./0.1 mm.

EXAMPLE 11

3-(o-Fluorophenoxy)-4-piperazinylpyridine

By substituting 2.26 g of 4-chloro-3-(o-fluorophenoxy)pyridine for the 4-chloro-3-phenoxypyridine and n-butanol for methanol of Example 1, the product is 3-(o-fluorophenoxy)-4-piperazinyl pyridine; bp 125°–127° C./0.1 mm.

EXAMPLE 12

3-(o-Chlorophenoxy)-4-piperazinylpyridine

By substituting 4 g of 4-chloro-3-(o-chlorophenoxy)-pyridine for the 4-chloro-3-phenoxypyridine and n-butanol for the methanol of Example 1, the product is 3-(o-chlorophenoxy)-4-piperazinylpyridine; mp 99°–101° C. after trituration with ether.

EXAMPLE 13

3-(m-Chlorophenoxy)-6-piperazinylpyridine

By substituting 5.5 g of 6-chloro-3-(m-chlorophenoxy)pyridine for the 6-chloro-3-phenoxypyridine and 11 g of piperazine for the β-diethylaminoethylamine of Example 3, the product is 3-(m-chlorophenoxy)-6-piperazinylpyridine; mp 70°–73° C. after recrystallization from anhydrous ether.

EXAMPLE 14

3-(p-Chlorophenoxy)-6-piperazinylpyridine

By substituting 4 g of 6-chloro-3-(p-chlorophenoxy)-pyridine for the 6-chloro-3-phenoxypyridine and 11 g of piperazine for the β-diethylaminoethylamine of Example 3, the product is 3-(p-chlorophenoxy)-6-piperazinylpyridine; mp 98°–100° C. after recrystallization from anhydrous ether.

EXAMPLE 15

3-(o-Fluorophenoxy)-6-piperazinylpyridine monohydrochloride

By substituting 3 g of 6-chloro-3-(o-fluorophenoxy)-pyridine for the 6-chloro-3-phenoxypyridine and 6 g of piperazine for the β-diethyl-aminoethylamine of Example 3, the product is 3-(o-fluorophenoxy)-6-piperazinylpyridine, bp 140°–150° C./0.1 mm.

A solution of this free base in 2-propanol is treated with an excess of hydrogen chloride dissolved in 2-propanol. Excess hydrogen chloride is removed by treatment with an excess of ethylene oxide. The mixture is concentrated in vacuo and the precipitate is collected by filtration to give 3-(o-fluorophenoxy)-6-piperazinylpyridine monohydrochloride, mp 187°–189° C. after recrystallization from 2-propanol.

EXAMPLE 16

3-(o-Chlorophenoxy)-2-(β-diethylaminoethylamino)-pyridine

By substituting 3.3 g of 2-chloro-(o-chlorophenoxy)-pyridine for the 2-chloro-3-phenoxypyridine and 16 g of β-diethylaminoethylamine for the piperazine of Example 2, the product is 3-(o-chlorophenoxy)-2-(β-diethylaminoethylamino)pyridine; bp 135°–142° C./0.1 mm.

EXAMPLE 17

4-(β-diethylaminoethylamino)-3-phenoxypyridine

By substituting 23 g of β-diethylaminoethylamine for the piperazine and n-butanol for the methanol of Example 1, the product is 4-(β-diethylaminoethylamino)-3-phenoxypyridine; bp 105°–108° C./0.13 mm.

EXAMPLE 18

3-(o-Chlorophenoxy)-4-(β-diethylaminoethylamino)-pyridine

By substituting 5.8 g 4-chloro-3-(o-chlorophenoxy)-pyridine for the 4-chloro-3-phenoxypyridine and 28 g of β-diethylaminoethylamine for the piperazine and n-butanol for the methanol of Example 1, the product is 3-(o-chlorophenoxy)-4-(β-diethylaminoethylamino)-pyridine; bp 152°–160° C./0.15 mm.

EXAMPLE 19

3-(m-Chlorophenoxy)-4-(β-diethylaminoethylamino)-pyridine

By substituting 8 g of 4-chloro-3-(m-chlorophenoxy)-pyridine for the 4-chloro-3-phenoxypyridine and 10 g of β-diethylaminoethylamine for the piperazine of Example 1, the product is 3-(m-chlorophenoxy)-4-(β-diethylaminoethylamino)pyridine; bp 130°–158° C./0.1 mm. This material is purified by chromatography over alumina (Woelm, neutral) in 0.5% methanol-toluene. Pure product is found in the first eluate.

EXAMPLE 20

4-(β-Diethylaminoethylamino)-3-(o-fluorophenoxy)-pyridine

By substituting 6.3 g of 4-chloro-3-(o-flurorphenoxy)-pyridine for the 4-chloro-3-phenoxypyridine and 30 g of β-diethylaminoethylamine for the piperazine of Example 1, the product is 4-(β-diethylaminoethylamino)-3-(o-fluorophenoxy)pyridine; bp 143°–145° C./0.1 mm.

EXAMPLE 21

3-Phenoxy-5-piperazinylpyridine monohydrochloride

To a solution of 12 g of 3-phenoxy-5-piperazinylpyridine N-oxide and 0.5 g of dichloromethane in 100 ml of ethanol is added 1 g of 20% Palladium on charcoal. The suspension is shaken under a pressure of 50 pounds per square inch of hydrogen atmosphere until no further drop in pressure occurs. The solution is filtered and concentrated in vacuo to give 3-phenoxy-5-piperazinylpyridine monohydrochloride; mp 191°–192.5° C. dec.

EXAMPLE 22

| Pharmaceutical Composition containing 3-phenoxy-4-piperazinylpyridine | |
|---|---|
| Ingredient | Quantity |
| 3-Phenoxy-4-piperazinylpyridine dihydrochloride | 193 g |
| Lactose | 1038 g |
| Corn Starch | 39 g |
| Hydroxypropyl cellulose | 30 g |
| Magnesium stearate | 7 g |
| Ethanol-water 50:50 | qs |

The 3-phenoxy-4-piperazinylpyridine dihydrochloride, lactose and hydroxypropyl cellulose are blended and granulated with 50:50 ethanol water. The wet granulation is screened, dried and re-screened. The resulting dried granulation is blended with the magnesium stearate and the corn starch, and the mixture is compressed into 225 mg tablets using 11/32 inch standard concave punches. Yield equals approximately 6,000 tablets each containing 32.2 mg of 3-phenoxy-4-piperazinylpyridine dihydrochloride equivalent to 25 mg of 3-phenoxy-4-piperazinyl pyridine base.

Starting Materials

The reactive (i.e., 2,4 and 6) chloro-3-aryloxypyridines are readily separated by column chromatography on SiO$_2$ in toluene followed by elution with toluene and toluene-methanol (50:50).

Alternatively the 4'-chloro-3-aryloxypyridines can be prepared by the reaction of a phenol with 3-fluoro-4-nitropyridine-N-oxide in the presence of potassium carbonate, followed by treatment of the formed aryl ether with an excess of phosphorus trichloride. This is superior if only the 4'-chloroisomer is desired.

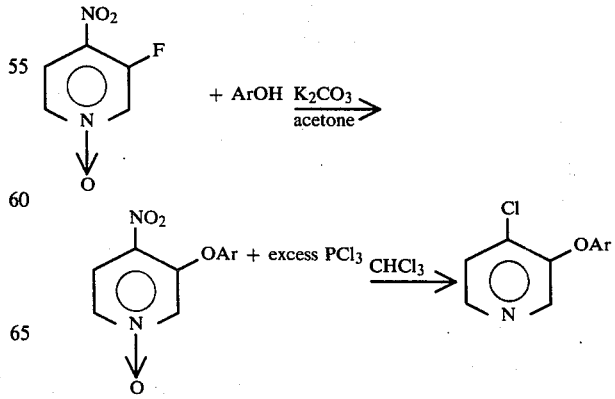

SYNTHESIS OF INTERMEDIATES TO EXAMPLES 1,2,3,5,6,7,8 and 17

2-Chloro-3-phenoxypyridine (for examples 2 and 6), 4-chloro-3-phenoxypyridine (for examples 1,5,7,8 and 17), 5-chloro-3-phenoxypyridine, and 6-chloro-3-phenoxypyridine (for example 3)

A solution of 18.6 g. of 3-phenoxypyridine N-oxide [J. Med. Chem., 14, 575 (1971)] in 50 ml of warm chloroform is dripped into 80 g of refluxing phosphorous oxychloride. The mixture is refluxed for 10 minutes and is concentrated in vacuo. The oil is dissolved in 500 ml of chloroform and washed with 40 ml of ice cold concentrated ammonium hydroxide. The organic phase is dried, concentrated in vacuo and distilled to yield the chlorinated mixture, bp 75°–90° C./0.1 mm. The mixture is dissolved in 50 ml of toluene and chromatographed over 400 g of silica gel in toluene. The 6-chloro-3-phenoxypyridine elutes first, bp 78°–80° C./0.1 mm and is readily identified by its proton magnetic resonance spectrum. A mixture of 2-chloro-3-phenoxypyridine and the unreactive 5-chloro-3-phenoxypyridine is eluted second, bp 82°–84° C./0.15 mm and is readily identified by its proton magnetic resonance spectrum. The 4-chloro-3-phenoxypyridine is eluted when the column is treated with toluene-methanol (50—50), bp 85°–87° C./0.2 mm.

INTERMEDIATE TO EXAMPLE 4

3-Bromo-6-piperazinylpyridine

A solution of 81.5 g of 2-piperazinylpyridine [J. Org. Chem., 18, 1484 (1953)] in 250 g of 48% hydrobromic acid is heated at 70° C. With stirring, 80 g of liquid bromine is added dropwise. The mixture is heated at 115° C. for 1 hour. The mixture is cooled and the product 3-bromo-6-piperazinylpyridine hydrobromide is isolated by filtration. The salt is treated with excess dilute sodium hydroxide and extracted into toluene. The 3-bromo-6-piperazinylpyridine crystallizes as the solvent is removed in vacuo and is recrystallized from toluene-petroleum ether; mp 70°–73° C.

INTERMEDIATES FOR EXAMPLE 9 AND 14

2-Chloro-3-(p-chlorophenoxy)pyridine (for example 9), 4-chloro-3-(p-chlorophenoxy)pyridine and 6-chloro-3-(p-chlorophenoxy)pyridine (for example 14)

A solution of 22 g of 3-(p-chlorophenoxy)pyridine N-oxide in 500 ml of chloroform is added dropwise to 77 g of refluxing phosphorous oxychloride. The mixture is refluxed 30 minutes, cooled and concentrated at reduced pressure. The resulting oil is dissolved in 400 ml of dichloromethane, washed with 40 ml ice cold concentrated ammonium hydroxide and the dichloromethane solution is dried over anhydrous $MgSO_4$. The mixture is filtered, concentrated under reduced pressure and distilled to yield the mixture of desired chlorinated pyridines; bp 103°–105° C./0.1 mm. The oil is dissolved in 100 ml of toluene and chromatographed over 400 g of silica gel in toluene to yield in the first eluate, 6-chloro-3-(p-chlorophenoxy)pyridine. Continued elution with toluene yields 2-chloro 3-(p-chlorophenoxy)pyridine. Finally, elution with toluene-methanol (50:50) yields 4-chloro-3-(p-chlorophenoxy)pyridine.

3-(p-chlorophenoxy)pyridine N-oxide

A solution of 93 g of 3-(p-chlorophenoxy)pyridine [Agr. Biol. Chem. 34, 68 (1970)] in 100 ml of glacial acetic acid is treated with 95 g of 40% peracetic acid in acetic acid in four equal portions. The mixture is heated at 35°–40° C. for 16 hours and than refluxed 1 hour. The mixture is cooled to 70° C.; 100 ml of isopropanol is added and the reaction heated at 95° C. for 2 hours. The mixture is concentrated in vacuo and dissolved in 700 ml of dichloromethane. The solution is washed with 25 ml of 25% cold sodium hydroxide solution, dried over anhydrous $MgSO_4$, concentrated at reduced pressure to yield crystalline 3-(p-chlorophenoxy)pyridine N-oxide, recrystallized from toluene; mp 138°–140° C.

INTERMEDIATES TO EXAMPLE 10,11,15 and 20

2-Chloro-3-(o-fluorophenoxy)pyridine (for example 10) 4-chloro-3-(o-fluorophenoxy)pyridine (for example 11 and 20) 6-chloro-3-(o-fluorophenoxy)pyridine (for example 15)

A solution of 25 g of 3-(o-fluorophenoxy)pyridine N-oxide in 50 ml of chloroform is added dropwise to 77 g of refluxing phosphorous oxychloride. The mixture is refluxed for 2 hours. The mixture is concentrated at reduced pressure. The oil is dissolved in 500 ml dichloromethane, washed with 50 ml of ice cold concentrated ammonium hydroxide and dried over anhydrous $MgSO_4$. The organic phase is separated, concentrated at reduced pressure and distilled to yield the mixture of desired chlorinated pyridines as an oil, bp 92°–105° C. at 0.1 mm. The oil is dissolved in 50 ml of toluene and chromatographed over 450 g of silica gel in toluene to yield in the first eluate 6-chloro-3-(o-fluorophenoxy)-pyridine. Continued elution with toluene yields 2-chloro-3-(o-fluorophenoxy)pyridine. Finally elution with toluene-methanol (50:50) yields 4-chloro-3-(o-fluorophenoxy)pyridine.

3-(o-fluorophenoxy)pyridine N-oxide

A solution of 30 g of 3-(o-fluorophenoxy)pyridine in 50 ml of glacial acetic acid is treated at 35° C. with 33 g of 40% peracetic acid in acetic acid in four portions. The mixture is stirred for 16 hours, refluxed 1 hour and 50 ml of isopropanol is added and the heating continued at 95° C. for 1 hour. The mixture is concentrated at reduced pressure and is dissolved in 300 ml of dichloromethane. The solution is washed with excess 25% sodium hydroxide solution. The dichloromethane solution is dryed over anhydrous $MgSO_4$, filtered and concentrated at reduced pressure. The 3-(o-fluorophenoxy)-pyridine N-oxide crystallizes, mp 89°–95° C.

3-(o-fluorophenoxy)pyridine

A solution of 100 g of o-fluorophenol in 50 ml of toluene is added to a suspension of 102 g of potassium t-butoxide in 400 ml of toluene. The mixture is concentrated at reduced pressure and 141 g of 3-bromopyridine plus 0.5 g of finely divided copper powder is added. The non-homogeneous mixture is heated to 165° C. by distillation of 20 ml of a low boiling liquid and held between 165° C. and 180° C. for 2 hours. The mixture is cooled, 700 ml of toluene is added and the mixture is filtered to remove inorganic salts. The organic layer is treated with an excess of 10% perchloric acid solution and the aqueous phase is separated. The aqueous phase is made strongly basic with excess 50% sodium hydroxide solution and extracted 3 times with 300 ml portions of toluene. The toluene extracts are combined, dried by distillation at atmospheric pressure and distilled to yield 3-(o-fluorophenoxy)pyridine, bp 127°–137° C. at 6 mm.

INTERMEDIATES FOR EXAMPLE 12 AND 18

4-Chloro-(3-o-chlorophenoxy)pyridine

A solution of 4.9 g of 3-(o-chlorophenoxy)-4-nitropyridine N-oxide in 200 ml of chloroform is cooled to −5° C. and a large excess of phosphorous trichloride is added. The mixture is stirred 1 hour at 0° C. and slowly warmed to 25° C. The solution is refluxed 1 hour, cooled, concentrated at reduced pressure and dissolved in 100 ml of dichloromethane. The solution is washed with 50 ml of ice-cold concentrated ammonium hydroxide. The solution is dried over anhydrous $MgSO_4$, filtered, concentrated at reduced pressure and distilled to yield 4-chloro-3-(o-chlorophenoxy)pyridine; bp 103°–105° C. at 0.1 mm.

3-(o-Chlorophenoxy)-4-nitropyridine N-oxide

A solution of 3.16 g of 3-fluoro-4-nitropyridine N-oxide [Rocz. Chem. 40, 1675 (1966), Chem. Abstr. 69, 59059d (1968)] and 2.58 g of o-chlorophenol in 250 ml of acetone is treated with 5.6 g of anhydrous potassium carbonate. The heterogeneous mixture is stirred vigorously at 25° C. for 16 hours. The mixture is filtered and concentrated at reduced pressure. The product is dissolved in 200 ml of acetonitrile and chromatographed over neutral alumina. The eluate is concentrated at reduced pressure and 3-(o-chlorophenoxy)-4-nitropyridine N-oxide is recrystallized from methanol-diethyl ether; mp 129°–131° C.

INTERMEDIATES FOR EXAMPLES 13 AND 19

2-Chloro-3-(m-chlorophenoxy)pyridine, 4-chloro-3-(m-chlorophenoxy)pyridine (for example 19) and 6-chloro-3-(m-chlorophenoxy)pyridine (for example 13)

A solution of 22 g of 3-(m-chlorophenoxy)pyridine N-oxide in 15 ml of chloroform is added dropwise to 77 g of refluxing phosphorous oxychloride and the mixture is refluxed for 30 minutes. The mixture is cooled, concentrated at reduced pressure and is dissolved in 400 ml of dichloromethane. The solution is washed with 25 ml of ice-cold ammonium hydroxide, dried over anhydrous $MgSO_4$, filtered, concentrated and distilled to yield the mixture of chlorinated pyridine; bp 102°–116° C. at 0.1 mm.

The mixture is dissolved in 200 ml of toluene and chromatographed over 400 g of silica gel in toluene. The first eluate yields 6-chloro-3-(m-chlorophenoxy)pyridine. The second eluate yields 2-chloro-3-(m-chlorophenoxy)pyridine. 4-Chloro-3-(m-chlorophenoxy)pyridine is eluted using toluene-methanol, 50:50.

3-(m-Chlorophenoxy)pyridine N-oxide

A solution of 110 g of 3-(m-chlorophenoxy)pyridine [Agr. Biol. Chem., 34, 68 (1970)] at 35° C. in 125 ml of glacial acetic acid is treated with 112 g of 40% peracetic acid in acetic acid in four equal portions. The mixture is held at 27° C. for 16 hours and heated at reflux for 1 hour. The mixture is cooled to 70° C., 100 ml of isopropanol is added and the mixture is heated at 95° C. for 1 hour. The warm mixture is concentrated at reduced pressure, dissolved in 500 ml of dichloromethane and extracted with excess 25% sodium hydroxide solution. The dichloromethane is removed at reduced pressure and the 3-(m-chlorophenoxy)pyridine N-oxide is isolated by distillation; 150°–152° C. at 0.15 mm, mp 72°–75° C.

INTERMEDIATE FOR EXAMPLES 16

2-Chloro-3-(o-chlorophenoxy)pyridine (for example 16), 4-chloro-3-(o-chlorophenoxy)pyridine and 6-chloro-3(o-chlorophenoxy)pyridine A solution of 22 g of 3-(o-chlorophenoxy)pyridine N-oxide in 10 ml of chloroform is added dropwise to 77 g of refluxing phosphorous oxychloride and the mixture is refluxed 15 minutes, cooled and concentrated at reduced pressure. The oil is dissolved in 400 ml dichloromethane, washed with 40 ml ice-cold concentrated ammonium hydroxide and dried over anhydrous $MgSO_4$. The mixture is filtered, concentrated and distilled to yield the chlorinated pyridines; bp 90°–115° C. at 0.15 mm. The mixture of isomers is dissolved in 200 ml of toluene and chromatographed over 400 g of silica gel in toluene. The first eluate yields 6-chloro-3-(o-chlorophenoxy)pyridine and the second elute yields 2-chloro-3-(o-chlorophenoxy)pyridine. 4-Chloro-3-(o-chlorophenoxy)pyridine is eluted using toluene-methanol, 50:50.

3-(o-Chlorophenoxy)pyridine N-oxide

A solution of 74.3 g of 3-(o-chlorophenoxy)pyridine [Agr. Biol. Chem. 34, 68 (1970)] in 75 ml of glacial acetic acid at 35° C. is treated with 76 g of 40% peractic acid in acetic acid in three equal portions. The mixture is held at 35° C. for 16 hours, refluxed 1 hour, cooled to 60° C. and 75 ml of isopropanol is added. The mixture is refluxed for 1 hour, cooled and concentrated at reduced pressure. The oil is dissolved in 700 ml of dichloromethane, washed with excess 25% sodium hydroxide solution, concentrated at reduced pressure and distilled to yield 3-(o-chlorophenoxy)pyridine N-oxide, bp 150°–155° C. at 0.15 mm.

INTERMEDIATE FOR EXAMPLE 21

5-Piperazinyl-3-phenoxypyridine N-oxide

An intimate mixture of 43 g of piperazine with 26.6 g of 5-bromo-3-phenoxypyridine N-oxide [Agr. Biol. Chem., 34, 68 (1970)] is heated at 150° C. for five hours. The oil is concentrated at reduced pressure to remove excess piperazine. The mixture is dissolved in 1500 ml of dichloromethane, washed with excess 25% sodium hydroxide solution, dried over anhydrous $MgSO_4$, filtered and concentrated to yield 5-piperazinyl-3-phenoxypyridine N-oxide as an oil. The oil is dissolved in 200 ml of toluene-methanol, (95-5) and chromatographed over 400 g, silica gel in toluene-methanol, (95-5). 5-Bromo-3-phenoxy-pyridine N-oxide is eluted first. Elution with toluene-methanol (50:50) yields 5-piperazinyl-3-phenoxypyridine N-oxide; mp 107°–115° C. after drying at 0.1 mm pressure for 16 hours.

I claim:

1. A compound of the formula

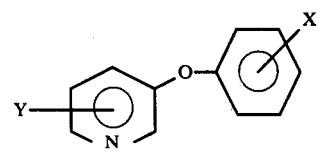

and pharmaceutically acceptable acid addition salts thereof; where X is hydrogen, fluorine or chlorine and Y is 1-piperazinyl, 3-methyl-1-piperazinyl, hexahydro- 2-methyl-1-H-1, 4-diazepin-1-yl, anilino, or 2[di(lower alkyl)amino] ethylamino.

2. The compounds of claim 1 wherein X is hydrogen, Y is piperazinyl, diethylaminoethylamino or anilino and the Y substituent is in the 4 or 2 position.

3. A compound of claim 1 having the name 3-phenoxy-4-piperazinylpyridine and pharmaceutically acceptable acid addition salts thereof.

4. A compound of claim 1 having the name 3-phenoxy-2-piperazinylpyridine and pharmaceutically acceptable acid addition salts thereof.

5. A compound of claim 1 having the name 4-($\beta$-diethylaminoethylamino)-3-phenoxypyridine and pharmaceutically acceptable acid addition salts thereof.

6. A compound of claim 1 having the name 3-(m-chlorophenoxy)-4-($\beta$-diethylaminoethylamino)pyridine and pharmaceutically acceptable acid addition salts thereof.

7. A compound of claim 1 having the name 3-Phenoxy-6-piperazinylpyridine and pharmaceutically acceptable acid addition salts thereof.

8. A compound of claim 1 having the name 2-anilino-3-phenoxypyridine and pharmaceutically acceptable acid addition salts thereof.

* * * * *